United States Patent [19]

Dittmer et al.

[11] Patent Number: 4,935,451

[45] Date of Patent: Jun. 19, 1990

[54] CONVERSION OF OPTICALLY ACTIVE EPOXY ALCOHOLS TO ALLYLIC ALCOHOLS

[75] Inventors: Donald C. Dittmer; Robert P. Discordia, both of Syracuse, N.Y.

[73] Assignee: Syracuse University, Syracuse, N.Y.

[21] Appl. No.: 405,684

[22] Filed: Sep. 11, 1989

[51] Int. Cl.$^5$ .................. C07C 29/74; C07C 29/00; C07C 33/03

[52] U.S. Cl. ................................ 568/908; 549/556

[58] Field of Search ........................................ 568/908

[56] References Cited

U.S. PATENT DOCUMENTS

| | | | |
|---|---|---|---|
| 4,471,130 | 9/1984 | Katsuki et al. | 549/523 |
| 4,594,439 | 6/1986 | Katsuki et al. | 549/529 |

FOREIGN PATENT DOCUMENTS

| | | | |
|---|---|---|---|
| 29603 | 6/1981 | European Pat. Off. | 568/908 |
| 157307 | 12/1975 | Japan | 568/908 |
| 164129 | 12/1981 | Japan | 568/908 |

OTHER PUBLICATIONS

Polson et al., Functional Group Modification via Organotellurium Chemistry, Tetrahedron Letters, V. 27, p. 5579 (1986).

Discordia et al., 2-Substituted-4-Hydroxymethyltellurophenes, Tetrahedron Letters, V. 29, p. 4923 (1988).

Barton et al., Sodium Hydrogen Telluride as a Useful Nucleophilic Reagent, Tetrahedron Letters, V. 26, p. 6197 (1985).

Clive et al., Alkali Metal O, O-Diethyl Phosphorotelluroates, 45 J. Org. Chemistry 2347 (1980).

Polson et al., Some New 3-Substituted 3-Hydroxyselenetanes, 53 J. Org. Chemistry 791 (1988).

Primary Examiner—J. E. Evans
Attorney, Agent, or Firm—Wall and Roehrig

[57] ABSTRACT

A two step procedure converts an epoxide residue from a Sharpless kinetic resolution of secondary allyl alcohols into an allyl alcohol of the desired chirality. The Sharpless system selectively epoxidizes one enantiomer of the allyl alcohol and leaves the other substantially unreacted. Then the epoxy alcohol is treated with methanesulfonyl anhydride and converted to epoxy mesylate. This product is contacted with a telluride salt in aqueous solution to convert it to the desired allyl alcohol with the chiral center inverted. This technique effects nearly complete conversion of racemic starting material to a single desired enantiomer.

7 Claims, No Drawings

CONVERSION OF OPTICALLY ACTIVE EPOXY ALCOHOLS TO ALLYLIC ALCOHOLS

BACKGROUND OF THE INVENTION

The usefulness of many pharmaceuticals and other biologically active agents, such as insect pheromones, depends critically on the fact that the molecules have a chiral atom of one specific chirality. However, any commercial synthesis of these compounds produces a racemic mixture of the compound produced with half the product of the desired chirality, and half of the opposite chirality. That is, when achiral molecules are resolved the two enantiomers are separated per chiral atom, each of opposite chirality. In commercial synthesis processes that utilize chiral allyl alcohols, the molecules whose chirality is opposite to that desired is of no use, and in some cases can be detrimental.

In a procedure described in Katsuki et al. U.S. Pat. Nos. 4,471,130 and 4,594,439 secondary allyl alcohols are converted from a racemic mixture to a single enantiomer of the desired chirality. This process is called Sharpless kinetic resolution. The enantiomer of the opposite chirality is converted to an epoxy alcohol whose carbinol carbon atom has the opposite configuration. This produces a substantially pure yield of the desired enantiomer, which amounts to about 50% of the racemic mixture. The other enantiomer, converted to an epoxy alcohol, may be of little value in the synthesis of a specific pheromone or other biological agent.

OBJECTS AND SUMMARY OF THE INVENTION

It is an object of this invention to convert the epoxy alcohol obtained in the foregoing procedure to the chiral allyl alcohol obtained in that procedure, thus effecting, in high yield and high stereospecificity, a conversion of a racemic allyl alcohol to a single enantiomer.

It is another object to provide a simple and straightforward technique to convert epoxy alcohols, whose chiral centers have an undesired chirality, to allyl alcohols of the desired chirality.

In accordance with one aspect of this invention, the chiral epoxy alcohol that results from the procedure described in U.S. Pat. Nos. 4,471,130 and 4,594,439 is converted in a two-stage process to allyl alcohol of the desired chirality. The racemic allyl alcohol is kinetically resolved by means of a titanium alkoxide or an equivalent catalyst. This selectively epoxidizes the enantiomer of the undesired chirality and leaves the allyl alcohol of the desired chirality substantially unreacted. The epoxy alcohol and the allyl alcohol can be physically separated.

The epoxide that results from this reaction is converted back to the allyl alcohol but with its chiral center inverted to the desired chirality. The epoxy alcohol is converted to an epoxy mesylate by action of methanesulfonyl anhydride in a suitable carrier, e.g. methylene chloride in which pyridine is also present. The resulting epoxy mesylate is then converted to the desired allyl alcohol by contacting it with aqueous sodium telluride. Any other soluble telluride salt could be employed. The active ion here should be a chalcogen heavier than sulfur, i.e., selenium or tellurium. By action of the tellurium ions the chiral center is inverted, so that the allyl alcohol product has the same chirality as the allyl alcohol produced by kinetic resolution as practiced above. Thus, the efficiency of the synthesis of the desired enantiomer is improved by substantially 100% over the prior art procedure.

The tellurium precipitates out in elemental form, and can be reused in subsequent reactions.

The above and many other objects, features, and advantages of this invention will be more fully understood from the ensuing description of a preferred embodiment, which is offered as an example.

DETAILED DESCRIPTION OF THE PREFERRED EMBODIMENT

This invention has been applied in connection with the so-called Sharpless kinetic resolution, that is the technique of Sharpless and Katsuki as described in U.S. Pat. Nos. 4,594,439 and 4,471,130, as well as elsewhere in the literature.

By combining the high yields and high selectivity of the Sharpless kinetic resolution with the high degree of stereoinversion, via telluride, of the chiral center, this invention achieves an easy three-step procedure to convert racemic secondary allyl alcohols to a single enantiomer without incurring a 50% loss of material as one does in pure Sharpless resolutions.

As an example, one gram of a racemic secondary allyl alcohol (prepared from the condensation of methacrolein with butyl lithium) was subjected to the Sharpless kinetic resolution that invoked (+)-DIPT (diisopropyl tartrate). The reaction was stopped at 50% completion as determined by capillary gas chromatography.

In the case of slow reacting allyl alcohols, i.e. reaction times on the order of two weeks, aliquots from the reaction can be reacted with Mosher chloride and analyzed by $^1$H NMR. These reactions are generally stopped when the enantiomeric excesses of the allyl alcohol and the epoxy alcohol are the same. A third way to stop the reaction at 50% completion is to supply only 0.5 equivalents of TBHP to the reaction mixture. This technique is only useful, however, on fast reacting allyl alcohol since the decreased amount of TBHP slows the reaction rate considerably.

The resulting mixture was separated, the allyl alcohol which was formed in 91% yield based on 50% conversion was put aside and the epoxy alcohol was converted to its sulfonate derivative with mesyl anhydride and pyridine in methylene chloride. The mesylate was then treated with the telluride ion, and the allyl alcohol was obtained in 97% yield for the two steps. The allyl alcohols from the two steps were combined (902 mg), 90% overall, 94% enantiomeric excess:

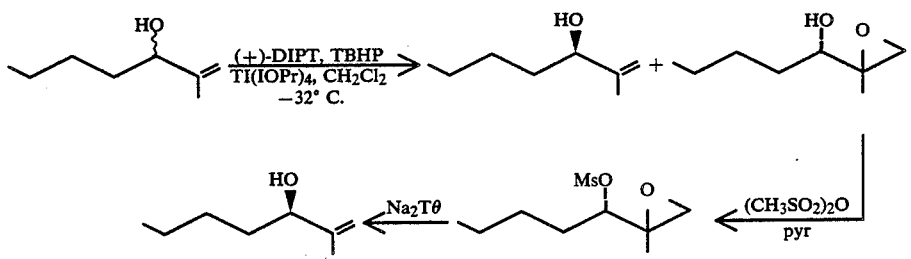

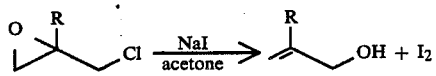

Here the notation of a wedge indicates that the attached radical projects from the plane of the page, the broken line indicates that the attached radical recedes behind the plane of the page, and the wavy line indicates a racemic mixture of both enantiomers.

The enantiomeric excess was determined by conversion of 20 mg of the allyl alcohol to its Mosher ester with Mosher acid and DCC (dicyclohexylcarbodiimide) in methylene chloride. $^1$H NMR analysis of the esters in CDCl$_3$ at 300 MHz (integrations ±2%) focused on the methine proton of the respective compounds. In the case of the secondary allylic alcohol, these protons were typically observed as a diastereomeric pair of AB doublets between 4.0 and 4.6 PPM. The epoxy ester's methine protons appear as an AB doublet between 3.6 and 3.9 PPM. $^{19}$F NMR integration of the absorption of the diastereomeric trifluoromethyl groups was also employed.

A similar procedure has also been employed to prepare allyl alcohols from epichlorohydrins by reaction of these compounds with sodium iodide in acetone. The reaction appears to open the ring via nucleophilic attack of iodide. The resulting intermediate iodomethyloxirane subsequently undergoes a halophilic attack by iodide ion to form the olefin and an equivalent of iodine.

Another example of the synthesis of single-enantiomeric allylic alcohol is as follows:

(±)-2-Methyl-1-hepten-3-ol: A 250-mL, three-necked round-bottomed flask was charged with dry nitrogen and n-butyllithium (62 mL, 2.5 M in hexane, 156 mmol) and was cooled to −30° C. Methacrolein (9.86 g, 141 mmol) in THF (50 mL) was added by addition funnel over a 1 h period with good stirring (overhead). The progress of the reaction was followed by TLC and was complete in 2 h. The reaction mixture was acidified with dilute, aqueous, ammonium chloride and the layers are separated. The aqueous layer was extracted with ether (3×30 mL) and the combined organic extracts were washed with water (2×20 mL). The organic layer was dried over sodium sulfate, filtered and the solvent removed by rotary evaporator to give a clear yellow oil. The oil was purified by distillation (kugelrohr) followed by flash chromatography (20:1 hexanes:ether) to give a clear colorless oil (13.9 g, 109 mmol, 77%).

Sharpless kinetic resolution of (±)-2-methyl-1-hepten-3-ol: A 100 mL three-necked round-bottomed flask was charged with (+) diisopropyl tartrate (0.37 g, 1.56 mmol), titanium (IV) isopropoxide (0.22 g, 0.78 mmol) and powdered and activated 3A molecular sieves (250 mg) and was cooled to −20° C. t-Butyl hydroperoxide (1.5 mL, 5.13 M in CH$_2$Cl$_2$, 7.8 mmol) was added in a minimal amount of solvent. The reaction's progress was followed by capillary GC and at exactly 50% completion was quenched into an ice cold aqueous FeSO$_4$/citric acid solution (20 mL of a stock solution; 33 g FeSO$_4$·7H$_2$O, 11 g citric acid in a total volume of 100 mL of water. The mixture was allowed to cool without stirring for 0.5 h. The layers were separated and the aqueous phase was extracted with methylene chloride (3×20 mL). The organic phase was concentrated to the original volume and the mixture was treated with sodium hydroxide in saturated brine for 1 h at 0° C. The layers were separated, and the aqueous layer was extracted with methylene chloride (3×20 mL), and the combined organic layers were washed with water (1×20 mL) and aqueous brine (2×20 mL). The organic layer was then dried over sodium sulfate, filtered and the solvent removed by rotary evaporator to yield a clear, colorless oil. The two compounds were then separated on silica gel (20% ether in hexanes). The allyl alcohol was obtained as a clear, colorless oil (455 mg, 3.56 mmol, 91.3% yield based on 50% conversion, 94% determined by NMR analysis of Mosher ester). Spectra were identical to those of the racemate. The epoxy alcohol was obtained as a clear, colorless oil (518 mg, 3.60 mmol, 92% yield based on 50% conversion, 94% ee).

Mesylation of 1,2-epoxy-3-hydroxy-2-methylheptane: The epoxy alcohol (511 mg, 3.55 mmol), methanesulfonyl anhydride (825 mg, 4.7 mmol) and pyridine (379 mg, 4.8 mmol) were dissolved in methylene chloride (25 mL) and were allowed to react for 1 h. The mesylate hydrolyzed on TLC. At completion, water was added to the reaction, the white precipitate dissolved and two distinct layers were formed. The layers were separated and the aqueous phase was extracted with methylene chloride (2×10 mL). The combined organics were washed with water (1×10 mL) and saturated aqueous brine (2×10 mL). The organic layers were then dried over sodium sulfate and the solvent removed by a rotary evaporator to leave a slightly yellow oil (775 mg, 3.5 mmol, 97%). The mesylate was used without further purification.

Formation of (R)-(+)-2-methyl-1-hepten-3-ol by sodium telluride: Sodium telluride was prepared using tellurium (670 mg, 5.3 mmol), sodium hydroxymethanesulfinate (2.41 g, 15.7 mmol), and NaOH (31 mL of a 1N aqueous solution, 31.4 mmol). To a room temperature solution of the sodium telluride there was added the epoxy mesylate (775 mg, 3.5 mmol) in THF (10 mL). After 1 h the reaction was opened to air and a stream of air was bubbled into the reaction. The reaction mixture was filtered through a plug of Celite to remove most of the tellurium metal. The filter pad was washed with ether until the filtrate was colorless. The filtrate was transferred to a separatory funnel and the organic phase was separated. The aqueous layer was extracted with ether (3×20 mL). The combined organic extracts were washed with dilute hydrogen peroxide (3% by volume, 2×20 mL). The solution became clear and colorless. The organic phase was then washed with water (2×20 mL) and with dilute sodium thiosulfate (2×10), dried over sodium sulfate, and the solvent was removed by rotary evaporator to leave a clear, colorless oil (447 mg, 3.49 mmol, i.e., substantially 100%). This product was then combined with the allyl alcohol form the Sharpless kinetic resolution, for a yield of 902 mg total combined weight, or 90% overall efficiency for three steps, and 94% ee determined by Mosher ester and by rotation.

General procedure for preparation of Mosher esters: The epoxy alcohol or the allyl alcohol (0.14 mmol) was dissolved in methylene chloride (2 mL) under nitrogen and cooled to 0° C. The mixture was treated with dicyclohexylcarbodiimide (43 mg, 0.21 mmol), DMAP (1 mg), and (R)-(+)-α-methoxy-α-(trifluoromethyl)-phenylacetic acid (Mosher acid) (40 mg, 17 mmol). A white, chalky precipitate was formed and the reaction was monitored by thin layer chromatography (TLC). The resulting mixture at completion was passed through a plug of silica with hexanes and the solvent was removed by rotary evaporator. The ester were then subjected to $^{19}F$ and $^{1}H$ NMR and the ratios of the diastereomers were determined by their respective integrations. Mosher esters can also be formed by the action of Mosher chloride in pyridine and $CH_2Cl_2$. These reactions are complete in about five minutes. Mosher chloride can be prepared from commercially available Mosher acid by the action of oxalyl chloride in the presence of a catalytic amount of DMF in methylene chloride. The process of our invention can be broadly summarized as follows, where R and R' are any groups:

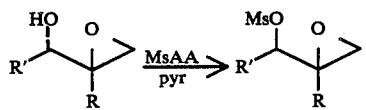

STEP 1

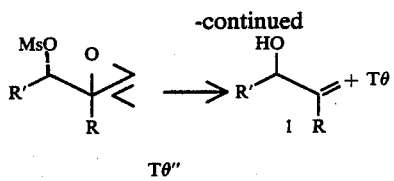

STEP 2

While the invention has been described in detail with reference to a preferred embodiment, the invention is not to be limited to that precise embodiment. Rather many modifications and variations would present themselves to those of skill in the art without departing from the scope and spirit of this invention, as defined in the appended claims.

What is claimed is:

1. A process of converting a chiral secondary epoxy alcohol to an allyl alcohol of a chirality opposite in sense to that of the carbinol center of the epoxy alcohol, comprising the steps of:
   introducing methanesulfonyl anhydride in a suitable carrier into said secondary epoxy alcohol to form an epoxy mesylate,
   separating the epoxy mesylate, and
   contacting the epoxy mesylate with a salt of an element selected from the group that consists of Se and Te to form said allyl alcohol.

2. The process of claim 1 wherein said salt is a telluride.

3. The process of claim 1 wherein said salt is introduced in an aqueous solution.

4. The process of claim 1 wherein said suitable carrier includes methylene chloride.

5. The process of claim 4 further including pyridine in said methylene chloride with said methanesulfonyl anhydride.

6. A process of converting a racemic mixture of a secondary allyl alcohol into allyl alcohol having substantially a single, desired chirality, comprising the steps of:
   selectively epoxidizing one enantiomer of the racemic allyl alcohol while leaving the remaining allyl alcohol enantiomer substantially unreacted, said remaining alcohol having said desired chirality,
   separating the resulting epoxy alcohol,
   reacting the epoxy alcohol with a methanesulfonyl anhydride in a suitable carrier to form an epoxy mesylate,
   separating the epoxy mesylate, and
   contacting the epoxy mesylate with a salt of an element selected from the group that consists of Se and Te to produce said allyl alcohol with said desired chirality.

7. The process of claim 6 wherein said salt includes a telluride in aqueous solution.

* * * * *

UNITED STATES PATENT AND TRADEMARK OFFICE
CERTIFICATE OF CORRECTION

PATENT NO. : 4,935,451
DATED : June 19, 1990
INVENTOR(S) : Donald C. Dittmer et al.

It is certified that error appears in the above—identified patent and that said Letters Patent is hereby corrected as shown below:

Col. 3, line 10,"Tθ" should read Te.

Col. 6, lines 1 - 8 please replace the entire Step 2 with the following:

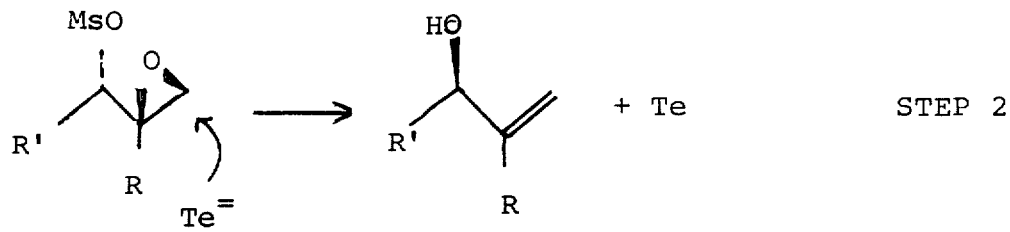

Signed and Sealed this

Seventh Day of April, 1992

*Attest:*

HARRY F. MANBECK, JR.

*Attesting Officer*     *Commissioner of Patents and Trademarks*